US009775340B2

(12) United States Patent
Piccolo et al.

(10) Patent No.: US 9,775,340 B2
(45) Date of Patent: Oct. 3, 2017

(54) BIOLOGICALLY ACTIVE FORMULATION

(75) Inventors: Oreste Piccolo, Sirtori (IT); Valerio Borzatta, Bologna (IT); Giovanna Delogu, Sassari (IT); Elisa Capparella, Ravenna (IT); Cristina de Candia, Sassari (IT); Carlotta Gobbi, Ravenna (IT); Giovanna di Blasi, Castel Maggiore (IT)

(73) Assignee: ENDURA S.P.A., Bologna (IT)

( * ) Notice: Subject to any disclaimer, the term of this patent is extended or adjusted under 35 U.S.C. 154(b) by 1308 days.

(21) Appl. No.: 11/912,136

(22) PCT Filed: Apr. 21, 2006

(86) PCT No.: PCT/EP2006/061724
§ 371 (c)(1),
(2), (4) Date: Oct. 19, 2007

(87) PCT Pub. No.: WO2006/111570
PCT Pub. Date: Oct. 26, 2006

(65) Prior Publication Data
US 2009/0130155 A1 May 21, 2009

(30) Foreign Application Priority Data
Apr. 22, 2005 (IT) .............................. MI2005A0729

(51) Int. Cl.
A01N 43/04 (2006.01)
C08B 30/18 (2006.01)
C08B 37/16 (2006.01)
A01N 25/10 (2006.01)

(52) U.S. Cl.
CPC .................................. A01N 25/10 (2013.01)

(58) Field of Classification Search
CPC ........ A01N 31/16; A01N 43/30; A01N 43/40; A01N 43/42; A01N 43/50; A01N 43/54; A01N 43/56; A01N 43/58; A01N 43/60; A01N 43/72; A01N 43/78; A61K 47/40
USPC ........ 514/58, 85, 249, 229.2, 248, 275, 341, 514/357, 365, 370, 407, 411, 464, 720
See application file for complete search history.

(56) References Cited

U.S. PATENT DOCUMENTS

| 4,056,610 | A   | 11/1977 | Barber, Jr. et al. |           |
|-----------|-----|---------|--------------------|-----------|
| 4,524,068 | A   | 6/1985  | Szejtli et al.     |           |
| 4,936,901 | A   | 6/1990  | Surgant, Sr. et al.|           |
| 5,238,682 | A * | 8/1993  | Akasaka et al.     | 424/409   |
| 5,707,638 | A * | 1/1998  | Losel et al.       | 424/407   |
| 6,448,262 | B1* | 9/2002  | Wood ............   | 514/301   |
| 6,896,892 | B2* | 5/2005  | Mount et al.       | 424/411   |

FOREIGN PATENT DOCUMENTS

| DE | 24 11 373 A1    | 9/1975  |
| DE | 37 08 671 A1    | 9/1987  |
| EP | 0 282 706 A     | 9/1988  |
| GB | 1 513 614 A     | 6/1978  |
| WO | WO 97/14308 A   | 4/1997  |
| WO | WO 03/092378 A  | 11/2003 |
| WO | WO 2005/039287 A2 | 5/2005 |

OTHER PUBLICATIONS

Casida et al. "Methylene-C Dioxyphenyl Compounds Metabolism in Relation to their Synergistic Action" 1966 (Casida I.*
Casida "Mixed-Function Oxidase Involvement in Biochemistry of Insecticide Synergists" 1970 (Casida II).*
Szekely et al. "MB-599 A new Synergist in Pest Control" 1996.*
Database WPI Section Ch, Week 199003 Derwent Publications Ltd., London, GB; An 1990-019276 XP002322687 & JP 01 299203 A, Dec. 4, 1989.
Biebel, R. et al. (2003) "Action of pyrethrum-based formulations against weevils" International Journal of Pharmaceutics 256:175-181.
Lajos, S. et al. (1990) "Formulation of insect controlling agents with B-cyclodextrin" Pesticide Science, Elsevier Applied Science Publisher. Barking, GB, 28:7-16.
Benchaoui, H.A. and Mckellar, Q.A. 1996 "Interaction between Fenbendazole and Piperonyl Butoxide: Pharmacokinetic and Pharmacodynamic Implications" *J Pharm Pharmacol* 48:753-759.
Finch, C.A. 1993 "Industrial Microencapsulation: Polymers for Microcapsule Walls" *Special Publication Rolay Soc Chem* 138:1-12.
Gimeno, M. 1996 "An Overview of the Latest Development of Microencapsulation for Agricultural Products" *J. Environ. Sci. Health*, B31(3):407-420.
Gunning, R.V. et al. 1998 in *Piperonyl Butoxide*, Chapter 13, "Inhibition of Resistance-related Esterases by Piperonyl Butoxide in *Helicoverpa armigera* (Lepidoptera: Noctuidae) and *Aphis gossypii* (Hemiptera: Aphididae)" Academic Press pp. 215-226.

(Continued)

*Primary Examiner* — Robert A Wax
*Assistant Examiner* — Danah Al-Awadi
(74) *Attorney, Agent, or Firm* — Silvia Salvadori, P.C.; Silvia Salvadori

(57) ABSTRACT

The present invention provides a formulation characterized by the simultaneous presence in cyclodextrin based supramolecular complexes, of two components, one of which possesses insecticidal, acaricidal, fungicidal, snailcidal or vermicidal activity and the other possesses an activity synergistic with the first, enhancing its effectiveness. The biologically active substance is chosen from the following classes of chemical products: carbamates, organophosphates, thioureas, pentatomic or hexatomic heterocycles in which 1, 2 or 3 nitrogen atoms are present. The synergistic substance can be chosen from components containing at least one aromatic or non aromatic carbocyclic ring, such as piperonyl butoxide, sesamol, verbutin or MGK 264. For the same dose, the activity of the present formulations is greater than that of the mixture of the two active components alone or separately complexed with cyclodextrin. The process for preparing said formulation and its use for the activities herein indicated are further aspects of the present invention.

20 Claims, No Drawings

(56) References Cited

OTHER PUBLICATIONS

Gunning R.V. et al. (1999) Esterase inhibitors synergise the toxicity of pyrethroids in Australian helicoverpa armigera (Hubner) (Lepidotera: Noctuidae) Pesticide Biochemistry ad Physiology 63:50-62.

Nishiwaki, H. et al. 2004 "Metabolism of Imidacloprid in House-flies" *J Pestic Sci* 29:110-116.

Wen, Z. and Scott, J.G. 1997 "Cross-Resistance to Imidacloprid in Strains of German Cockroach (*Blattella germanica*) and House Fly (*Musca domestica*)" *Pestic Sci* 49:367-371.

Zhao, J.-Z. et al. 2000 Inheritance and Synergism of Resistance to Imidacloprid in the Colorado Potato Beetle (*Coleoptera*: Chrysomelidae) *J Econ Entomology* 93:1508-1514.

\* cited by examiner

BIOLOGICALLY ACTIVE FORMULATION

RELATED APPLICATIONS

This application is a U.S. National Phase of International Application PCT/EP2006/061724, filed Apr. 22, 2006, designating the U.S. and published in English on Oct. 26, 2006 as WO 2006/111570, which claims the benefit of Italian Application No. MI2005A000729, filed Apr. 22, 2005.

FIELD OF THE INVENTION

The present invention relates to the field of insecticide, acaricide, fungicide, snailcide and vermicide compositions and in particular those in which the active principle is mixed with synergistic substances having various mechanisms of action, for example substances inhibitory to detoxification mechanisms in insects. New formulations are described in which the effect of the insecticide, acaricide, fungicide, snailcide and vermicide and synergistic substance is further enhanced to by formation of cyclodextrin based complexes.

PRIOR ART

The problem of tolerance and resistance to insecticidal, acaricidal, fungicidal, snailcidal and vermicidal activity is particularly serious and of growing importance, leading to the ever more difficult control and eradication of damaging species (insects, mites, moulds, snails, worms) so that protection against their action in agriculture, veterinary medicine, domestic hygiene and in manufactured articles becomes necessary.

Many damaging species have strengthened their natural defences and immune systems against the toxins with which they come into contact, so that to achieve their eradication, dosages have to be increased or new insecticides, acaricides, fungicides, snailcides or vermicides must be continually used with consequent greater risks and damage to the entire ecosystem and the overall food chain up to man, and with rising costs.

It is widely reported in the literature that the use of substances such as piperonyl butoxide (PBO) and its analogues, sesamol, verbutin, MGK 264 and DEF (S,S,S-tributyl phosphorotrithioate), can enhance insecticidal, acaricidal, fungicidal, snailcidal and vermicidal activity in vitro and/or in vivo, either by inhibiting the activity of certain insect metabolic enzymes involved in detoxification and resistance or by other mechanisms of action [see for example Gunning et al., "Piperonyl Butoxide", pages 215-225, Academic Press (1998); Nishiwaki, H. et al., *J. Pest. Sci.* 2004, 29, 110-116, Ahmad, M. et al., *Pest. Manag. Sci.* 2004, 60, 465-473, Li A. Y. et al., *J. Med. Entomol.* 2004, 41, 193-200, Sanchez, S. et al., *J. Vet. Pharmacol. Therap.,* 2003, 26 (suppl1), 197, Uesugi, Y. et al., *Agric. Biol. Chem.,* 1978, 42, 2181-2183 and the following patent applications: WO 94/17798, WO 00/02557, EP 830813].

In order to better demonstrate the synergistic activities, particularly in cases where the damaging species is most resistant, treatment with the synergistic product at different times prior to the active principle or a repeated treatment with active principle was proposed; pre-treatment with the synergistic compound is particularly beneficial in that subsequent exposure to the active principle occurs on the already sensitised damaging species, thus with weakened capacity to defend themselves, and is therefore more effective. Separate administrations however are not very practical and are economically unfavourable compared with a single application of the two components.

Also described in the literature and in patent applications are insecticide, acaricide, fungicide, snailcide and vermicide formulations in cyclodextrins (CD) [see for example Szente, L. et al, "Cyclodextrins in Pesticides", in "Comprehensive Supramolecular Chemistry", pages 503-514, Elsevier (1996); Castillo, J. A. et al., *Drug Develop. Ind. Pharm.* 1999, 25, 1241-1248; Lezcano, M. et al., *J. Agric. Food Chem.* 2002, 50, 108-112]. The main purposes of said supramolecular complexes are: modification of the physico-chemical properties of active principles without however altering their biological activity once the active principles are released, greater stability, increased wettability and bioavailability of poorly soluble and difficultly absorbable active principles, reduced environmental toxicity and reduced toxicity for operators.

The $\alpha,\beta,\gamma$ cyclodextrins are natural or semi-synthetic cyclic oligosaccharides, being generally non-toxic and biodegradable; $\beta$-CD, $\gamma$-CD and certain derivatives thereof such as hydroxypropyl-$\beta$-cyclodextrin (HP-$\beta$-CD) and sulfobutyl ether-$\beta$-cyclodextrin (SBE-$\gamma$-CD) are particularly preferred for applications.

Although some improvements in the insecticidal, acaricidal, fungicidal, snailcidal or vermicidal activity and physico-chemical properties of active principles have been described, when comparing the properties of active principles and their corresponding complexes with CD [see for example Kamiya, M. et al., *Chemosphere* 1995, 30, 653-660; Shehafta, I., *Monatsh. Chem.* 2002, 133, 1239-1247; Tanari, F. et al., *Inclus. Phenom. Macrocycl. Chem.* 2003, 46, 1-13], no formulation that simultaneously contains a synergistic compound has been previously reported to the best of our knowledge.

PBO has also been prepared in the form of a complex with CD (see U.S. Pat. No. 4,524,068) and found to be more effective as an insecticide synergist than uncomplexed PBO; again in this case the trials were carried out on mixtures of insecticides and PBO/CD and not on a single formulation as in the present invention. Furthermore, the process used in U.S. Pat. No. 4,524,068 was found not to be ideal for preparing a supramolecular complex containing the active principle and the synergistic compound simultaneously in CD. To the best of our knowledge complexes of other synergists with CD are not known, with the exception of a study on the formation and the physico-chemical properties of an inclusion complex of MGK 264 in $\beta$-CD (Szente, L. et al., *Pestic. Sci.,* 1990, 28, 7-16); this work, however, does not face problems similar to those of the present invention as said complex was not used in combination with biologically active substances.

The previous literature, even when combined, has therefore not provided the expert of the art with any useful information for preparing the innovative formulation of the present invention, nor has it suggested an effectiveness of said formulation surprisingly superior to that of a mixture of the individual components, either free or complexed with CD, on insecticidal, acaricidal, fungicidal, snailcidal or vermicidal activity for agricultural applications, for veterinary medicine use, for domestic hygiene or for the protection of manufactured articles. The present invention proposes to overcome the drawbacks of the known art and to significantly improve the performance of commercially known products with insecticidal, acaricidal, fungicidal, snailcidal or vermicidal activity.

SUMMARY

The present invention relates to an innovative formulation, characterised by the formation of a supramolecular complex in cyclodextrins of:
(i) an active principle consisting of a component with insecticidal, acaricidal, fungicidal, snailcidal or vermicidal activity
(ii) a component able to synergistically enhance the activity of the active principle. The formulation is obtained by jointly subjecting both an active principle and a synergistic compound to treatment with CD, under particular reaction conditions. By "supramolecular" complex it is meant a complex as defined for example in "Cyclodextrins in Pesticides" Comprehensive Supramolecular Chemistry 503-514, Elsevier, 1996). The invention also relates to the preparation of said formulation and to its use for eradicating damaging species in agriculture, in veterinary medicine, in domestic hygiene or in manufactured articles. The formulation is obtained by jointly subjecting both the active principle and the synergistic compound to supramolecular complex formation with CD.

The aforesaid formulation is also effective in cases where the damaging species demonstrate tolerance and resistance to treatment with the same active substance, and induces, for the same quantity of principle, a substantially higher mortality of the damaging species than that demonstrated by the same components i) and ii) used in a mixture as such or complexed separately with cyclodextrin.

DETAILED DESCRIPTION OF THE INVENTION

Any cyclodextrin can be used for the purposes of the present invention. For example the cyclodextrin can be α,β,γ cyclodextrin as such or suitably derivatized to increase its hydrophilic or hydrophobic character. Particularly preferred are β-CD, γ-CD and HP-β-CD. Usable active principles in the present invention belong to one of the following classes of chemical products: carbamates, organophosphates, thioureas, pentatomic or hexatomic heterocyles where 1, 2 or 3 nitrogen atoms are present, such as pyridine, pyrrole, imidazole, benzimidazole, thiazole, pyrazole, pyridazine, quinazoline, oxadiazine, triazine. Particularly preferred are neonicotinoids, such as Imidacloprid, Acetamiprid, Thiacloprid, Thiamethoxam and AKD1022, carbamates such as Pyrimicarb, Aldicarb, Thiodicarb, Carbosulfan, Carbofuran and Propoxur; organophosphates such as Profenofos, Dimethoate, Omethoate, Terbufos, Azinphos-methyl, Pyrimiphos-methyl, Demeton-s-methyl, Fenitrothion, Trichlorfon and Malathion; mitochondrial electron transport inhibitors ("METI") such as Fenazaquin, Tebufenpyrad, Fenpyroximate, Pyridaben and Tolfenpyrad; fungicides such as Fludioxonil, Clotrimazole, Imazalil and Pyrimethanil; vermicides such as Mebendazole, Metronidazole, Fenbendazole, Thiabendazole and Praziquantel; nerve transmission inhibitors such as Indoxacarb and Fipronil and other active principles in which the mechanism of action against damaging species is still uncertain or which have miscellaneous mechanisms, such as Pymetrozine, Chlorfenapyr and Pyridalyl. Even more preferred are: Imidacloprid, Acetamiprid, Thiacloprid, Thiodicarb, Carbosulfan, Carbofuran, Fenazaquin, Pyridaben, Fludioxonil, Pyrimethanil, Fenbendazole, Clotrimazole, Praziquantel, Fipronil, Pymetrozine and Pyridalyl.

The aforesaid preferred compounds can be subdivided on the basis of their activity as follows:

Insecticides: Imidacloprid, Acetamiprid, Thiacloprid, Thiamethoxam, AKD 1022, Pyrimicarb, Aldicarb, Thiodicarb, Carbosulfan, Carbofuran, Propoxur, Profenofos, Dimethoate, Omethoate, Azinphos-methyl, Pyrimiphos-methyl, Demeton S-methyl, Pyrimiphos-methyl, Demeton S-methyl, Fenitrothion, Trichlofon, Malathion, Pyridaben, Tolfenpyrad, Indoxacarb, Fipronil, Pymetrozine, Chiorphenapyr, Pyridalyl.

Acaricides: Dimethoate, Omethoate, Pyrimiphos-methyl, Demeton-5-methyl, Fenithrothion, Malathion, Fenazaquin, Tebufenpyrad, Fenpyroximate, Pyridaben.

Snailcides: Propoxur, Terbufos, Pyrimiphos-methyl, Fenitrothion, Trichlorfon, Malathion, Tolfenpyrad, Fipronil, Chlorphenapyr, Pyridalyl.

Vermicides: Carbosulfan, Carbofuran, Terbufos, Pyrimiphos-methyl, Fenithrotion, Trichlorfon, Malathion, Fipronil, Mebendazole, Metronidazole, Fenbendazole, Thiabendazole, Clotrimazole, Praziquantel.

Fungicides: Fludioxonil, Clotrimazole, Imazalil, Pyrimethanil.

The quantity of active principle relative to cyclodextrin is preferably between 1% and 50% (weight/weight) and even more preferably between 2% and 30%.

The components able to synergistically enhance active principle activity (referred to herein in brief as "synergistic compounds") are substances for se known and already in use. Preferred examples of synergistic compounds are piperonyl butoxide and its analogues, sesamol, verbutin and MGK264, piperonyl butoxide and verbutin being particularly preferred. Piperonyl butoxide is most preferred. The synergistic compounds can be used as such or already pre-formulated with additives; an example of a commercially available pre-formulation is marketed as PB80EC-NF, containing 88% PBO and 12% emulsifier (dialkylsulfosuccinate also known as SOITEM).

The quantity of synergistic compound relative to cyclodextrin is between 0.1% and 100% (weight/weight), preferably between 10% and 80% and even more preferably between 20% and 70%. These percentages refer to the quantity of pure synergistic compound, therefore excluding any additives present in the pre-formulation.

The quantity of active principle relative to the synergistic compound is between 0.5% and 7000% (weight/weight), preferably between 1% and 1500%, more preferably between 2% and 100% and even more preferably between 10% and 70%.

Emulsifiers, UV stabilizers, antioxidants and other additives can also be present in the aforesaid formulation.

The quantity of said additives relative to cyclodextrin is preferably between 0% and 30% (weight/weight), more preferably between 1% and 15%. These percentages refer to all the additives present, also including those already present in the pre-formulations of the active principles utilized.

Usable emulsifiers are for example dodecylbenzenesulfonate, dialkylsulfosuccinate, lignin sulfonates, phospholipids, polyethylene glycols. Usable UV stabilizers are for example 2-hydroxy-4-methoxy-benzophenone, 2-hydroxy-4-octoxy-benzophenone, 4-hydroxy-2,2,6,6-tetramethylpiperidine sebacate.

A usable antioxidant is for example 2,6-di-tert-butyl-1-hydroxy-toluene.

A microemulsified synergist can be optionally added to the formulations of the present invention, being the same as or different from that present in the supramolecular complex, in a quantity from 0% to 300% (weight/weight) relative to the cyclodextrin.

The composition of the invention is preferably formulated as a solid or as a solid/oil composition; said formulations can be utilised as such, or previously dissolved/emulsified in water or in aqueous solutions of water-miscible solvents, such as a C1-4 alcohol; said aqueous solutions contain 0%-99% by weight of organic solvent, preferably from 0-60% by weight of organic solvent.

The process for preparing the aforedescribed formulations is characterized by the formation of a supramolecular complex in cyclodextrins of the synergistic compound and the active principle having insecticidal, acaricidal, fungicidal, snailcidal or vermicidal activity.

More specifically the preparation process can be performed in accordance with one of the following methods, indicated as procedure A and procedure B respectively.

Procedure A:
(a) preparing a solution or suspension, in a suitable solvent, of the synergistic compound and the active principle optionally in the presence of a suitable surfactant, the latter being present in a quantity from 0% to 12%, preferable from 2% to 4% of the synergistic compound; the solvent is preferably an alcoholic solvent, e.g. ethanol or isopropanol;
(b) preparing a solution of cyclodextrin in water or in water/water-miscible organic solvent mixtures; the dissolution of the CD can conveniently be facilitated by heating (e.g. between 50° and 90° C., preferably between 70° C. and 80° C., for 30-90 minutes).
(c) adding the solution/suspension obtained in (a) to the solution obtained in (b); preferably the solution/suspension of (a) is added slowly, e.g. over 2-10 hours (more preferably over 4-8 hours), pre-heated to a temperature between 500 and 90° C., preferably between 500 and 75° C.;
(d) maintaining the mixture under agitation at a temperature between 40° and 90° C. (preferably between 50° and 75° C.) for a time period generally between 12 and 36 hours (preferably 18-24 hours).

The supramolecular complex of the synergistic compound and the active principle in CD is recovered from the reaction mixture by known methods, such as filtration, drying or lyophilization.

Procedure B
(a) dissolving the active principle in the synergistic compound, heating to a temperature preferably between 700 and 140° C., possibly in the presence of a suitable surfactant in a quantity up to 12%, preferably from 2% to 4% relative to the synergistic compound;
(b) preparing a suspension of cyclodextrin in water preferably using a percentage (weight/weight) of CD between 30% and 70% and heating the suspension to a temperature between 60° and 80° C.;
(c) adding the hot solution obtained in (a) to the hot suspension obtained in (b) over a time period between 10 and 600 minutes;
(d) maintaining the mixture under stirring at a temperature between 50° and 90° C. (preferably between 70° and 90° C.) for a time period generally comprised between 1 and 12 hours (preferably between 1 and 4 hours).

The supramolecular complex of the synergistic compound and the active principle in CD is recovered from the reaction mixture by filtration and subsequent drying. The complex thus formed can be mixed with the previously indicated possible additional components of said formulations; said optional components also include an additional quantity of synergistic compound in free form, being the same as or different from that present in the supramolecular complex; said components can be mixed with the supramolecular complex as solids or as microemulsions, immediately prior to use.

A further aspect of the invention is the use of the aforesaid formulations as insecticides, acaricides, fungicides, snailcides or vermicides in agriculture, for use in veterinary medicine, for eradicating household insects and for protecting manufactured articles. Formation of said supramolecular complex of the active principle and synergistic compound in CD has surprisingly led to a significant increase in composition effectiveness compared to the mixture of the two components used as such or complexed individually with cyclodextrin. By means of the invention an enhanced interaction between the active principle and the synergistic compound is achieved; in comparative trials undertaken by the inventors, said enhancement was always found to be greater than 50%.

Enhancement of activity leads to various advantages of industrial significance: for example for the same active substance used, more active synergistic compositions can be obtained; or compositions with an effectiveness equal to known compositions can be obtained but with lower amount of active substance; the lesser amount of active substance in use leads to reduced product cost, reduced environmental impact of the manufacturing process, as well as reduced volume/weight of the final composition, with further practical advantages for the operator using these formulations.

Consequently with the present invention insecticide, acaricide, fungicide, snailcide or vermicide formulations are unexpectedly obtained, which are highly effective and less costly than known formulations.

The following examples illustrate the invention without however in any way limiting it.

EXPERIMENTAL PART

Example 1

General Procedure for Preparing the Formulation According to Procedure A

The suitable CD in distilled water is introduced at 50°-90° C. into a 2-neck flask equipped with cooler and nitrogen outlet. The CD aqueous solution, with concentration between 2% and 15% by weight, for example at 10%, is left under stirring at the same temperature for 1 hour. After said period a solution in water soluble solvent containing the active principle and synergistic compound in the required proportions is added in portions over a 6-hour period. The mixture is maintained under stirring at 40°-90° C. for a further 12-36 hours, then the mixture is left to cool to ambient temperature under stirring and finally left to decant for 3-5 hours. The mixture is evaporated to dryness under vacuum. The supramolecular complexes thus obtained prove to be stable in the solid phase for at least 30 days at 23° C.

Example 2

Preparation of a Formulation Based on Acetamiprid and PBO

The βCD (2 g) in distilled water (20 ml) is introduced at 75° C. into a 2-neck flask, equipped with cooler and nitrogen outlet. The solution is left under stirring for 1 hour at 75° C. After this period a solution of isopropanol (25 ml) containing PBO/SOITEM (98/2, 0.536 g equal to 0.525 g of PBO and 0.011 g of SOITEM in total) and acetamiprid (0.115 g)

is added in portions over a 6-hour period. The mixture is maintained under stirring at 75° C. for a further 18 hours, then left to cool to ambient temperature under stirring over a 2-hour period and finally left to decant for 3 hours. The solution is evaporated under vacuum to a solid residue to provide 2.6 g of formulated product.

Example 3

Preparation of a Formulation Based on Imidacloprid and PBO

The βCD (2 g) in distilled water (20 ml) is introduced at 75° C. into a 2-neck flask, equipped with cooler and nitrogen outlet. The solution is left under stirring for 1 hour at 75° C. After said period a solution of isopropanol (25 ml) containing PBO/SOITEM (98/2, 0.536 g equal to 0.525 g of PBO and 0.011 g of SOITEM in total) and imidacloprid (0.134 g) is added in portions over a 6-hour period. The mixture is maintained under stirring at 75° C. for a further 18 hours, then left to cool to ambient temperature under stirring over a 2-hour period and finally left to decant for 3 hours. The solution is evaporated under vacuum to a solid residue to provide 2.4 g of formulated product.

Example 4

Preparation of a Formulation Based on Acetamiprid and PBO

Using the same method as described in example 2, a solution of isopropanol (22.5 ml) containing PBO/SOITEM (98/2) (0.0018 g equal to 0.0017 g of PBO and 0.0001 g of SOITEM) and 0.103 g of acetamiprid is slowly added to a solution of 1.8 g βCD in 18 ml of distilled water.

By following the aforegiven method, 1.9 g of formulated product are obtained.

Example 5

Preparation of a Formulation Based on Acetamiprid and PBO

Using the same method as described in example 2, a solution of isopropanol (25 ml) containing PBO/SOITEM (98/2) (0.01 g equal to 0.0098 g of PBO and 0.0002 g of SOITEM) and 0.115 g of acetamiprid is slowly added to a solution of 2.0 g γCD in 20 ml of distilled water.

By following the aforegiven method, 2.1 g of formulated product are obtained.

Example 6

Preparation of a Formulation Based on Imidacloprid and PBO

Using the same method as described in example 3, a solution of isopropanol (22.5 ml) containing PBO/SOITEM (98/2) (0.0018 g equal to 0.0017 g of PBO and 0.0001 g of SOITEM) and 0.12 g of imidacloprid is slowly added to a solution of 1.8 g βCD in 20 ml of distilled water.

By following the aforegiven method, 1.8 g of formulated product are obtained.

Example 7

Preparation of a Formulation Based on Imidacloprid and PBO

Using the same method as described in example 3, a solution of isopropanol (45 ml) containing PBO/SOITEM (98/2) (0.018 g equal to 0.017 g of PBO and 0.001 g of SOITEM) and 0.241 g of imidacloprid is slowly added to a solution of 3.6 g βCD in 36 ml of distilled water.

By following the aforegiven method 3.8 g of formulated product are obtained.

Example 8

Preparation of a Formulation Based on Thiabendazole and PBO

Using the same method as described in example 2, a solution of isopropanol (120 ml) containing PBO/SOITEM (98/2, 2.92 g equal to 2.87 g of PBO and 0.050 g of SOITEM in total) and thiabendazole (1.7 g) is slowly added to a solution of β-CD (14.4 g) in 120 ml of water. The mixture is maintained under stirring at 75° C. for a further 5 hours, then allowed to cool at about 40° C. and maintained at this temperature under stirring for 15 hours. Cooling at ambient temperature is then performed and the solution is dried under vacuum yielding 19.1 g of formulated product.

Example 9

Preparation of a Formulation Based on Fipronil and PBO

Using the same method as described in example 2a solution of isopropanol (120 ml) containing PBO/SOITEM (98/2, 3.87 g equal to 3.79 g of PBO and 0.077 g of SOITEM in total) and fipronil (1.6 g) is slowly added to una solution of β-CD (14.4 g) in 120 ml of water. The mixture is maintained under stirring at 75° C. for a further 5 hours, then it is allowed to cool at about 40° C. and maintained at this temperature under stirring for 15 hours. Cooling at ambient temperature is then performed, and the solution is dried under vacuum, yielding 19.7 of formulated product.

Example 10

General Procedure for Preparing the Formulation According to Procedure B

The suitable CD in distilled water is introduced at a temperature comprised between 20° and 30° C. into a 2-neck flask equipped with cooler and nitrogen outlet in weight/weight proportions preferably between 30% and 70%. The suspension is then heated to a temperature comprised between 60° and 80° C. and left under stirring at the same temperature for a convenient time period e.g. 10-30 minutes. After said period a preheated mixture of the active principle and synergistic compound in the required proportions are added in portions. The mixture is maintained at a temperature comprised between 70° and 90° C. under stirring for a further 1-2 hours then left to cool to ambient temperature under stirring. A solid is obtained by filtration which is then dried under vacuum.

The supramolecular complexes thus obtained prove to be stable in the solid phase for at least 30 days at 23° C.

Example 11

Preparation of a Formulation Based on Acetamiprid and PBO

βCD (13.9 g) in water (20 ml) is introduced into a 2-neck flask at 25° C. The mixture, consisting of a suspension, is left under stirring (300 rpm) for 15 minutes at 25° C. After this time the temperature is brought to 70° C., then a mixture of acetamiprid (0.802 g), PBO (3.65 g) and SOITEM (0.07 g) is added over a 2-hour period. The mixture is agitated for 1 hour at a temperature comprised between 70° and 80° C., then left to cool to ambient temperature. By means of filtration a white solid is obtained which is dried for 3 hours under vacuum (25° C./1 mbar) to provide 14.4 g of formulated product.

Example 12

Preparation of a Formulation Based on Imidacloprid and PBO

βCD (13.9 g) in distilled water (20 ml) is introduced into a 2-neck flask at 25° C. The mixture, consisting of a suspension, is left under stirring (300 rpm) for 15 minutes at 25° C. After this time the temperature is brought to 70° C., then a mixture of imidacloprid (0.933 g), PBO (3.65 g) and SOITEM (0.07 g) is added over a 2-hour period. The mixture is agitated for 1 hour at 90° C., then left to cool to ambient temperature. By means of filtration a white solid is obtained which is dried under vacuum (25° C./1 mbar) for 3 hours to provide 16.4 g of formulated product.

Example 13

Preparation of a Formulation Based on Diazinon and PBO

Using the same method as described in example 11, a formulation was prepared starting from β-CD (50 g) in distilled water (72 ml), diazinon (4 g) in a mixture with PBO (14.1 g) and SOITEM (0.3 g).

By following the previously reported procedure, 64 g of formulated product are obtained.

Example 14

Preparation of a Formulation Based on Imazalil and PBO

Using the same method as described in example 11, a formulation was prepared starting from of β-CD (25 g) in of distilled water (36 ml), imazalil (1.95 g) in a mixture with PBO (7 g) and SOITEM (0.15 g).

By following the previously reported procedure, 27.5 g of formulated product are obtained.

Example 15

Preparation of a Formulation Based on Fenazaquin and PBO

Using the same method as described in example 11, a formulation was prepared starting from β-CD (50 g) in distilled water (72 ml), fenazaquin (4.0 g) in a mixture with PBO (14 g) and SOITEM (0.3 g).

By following the previously reported procedure 58.2 g of formulated product are obtained.

Example 16

Preparation of a Formulation Based on Pyrimicarb and PBO

Using the same method as described in example 11, a formulation was prepared starting from β-CD (50 g) in distilled water (72 ml), pyrimicarb (3.1 g) in a mixture with PBO (13.2 g) and SOITEM (0.27 g).

By following the previously reported procedure 60.5 g of formulated product are obtained.

Example 17

Preparation of a Formulation Based on Pyridaben and PBO

Using the same method as described in example 11, a formulation was prepared starting from β-CD (50 g) in distilled water (72 ml) pyridaben (4.8 g) in a mixture with PBO (14.1 g) and SOITEM (0.3 g).

By following the previously reported procedure 64.2 g of formulated product are obtained.

Example 18

Preparation of a Formulation Based on Pyrimethanil and PBO

Using the same method as described in example 11, a formulation was prepared starting from β-CD (50 g) in distilled water (72 ml), pyrimethanil (2.6 g) in a mixture with PBO (14.1 g) and SOITEM (0.3 g).

By following the previously reported procedure 57.3 g of formulated product are obtained.

Example 19

Preparation of a Formulation Based on Imidacloprid and PBO

Hydroxypropyl β-cyclodextrin (10 g) in distilled water (250 ml) is introduced at room temperature into a two-neck flask provided with cooler and nitrogen outlet. Thereafter, a solution of PBO/SOITEM 98/2 p/p (4.4 g) and imidacloprid (1.0 g), in isopropanol (10 ml) is added. The solution is heated to 75° C. and is allowed to react at this temperature for 3 h, then the mixture is allowed to cool at room temperature under stirring. The mixture is dried under vacuum, yielding 15.3 g of formulated product.

Example 20

Mortality Assay (for Insecticide Compounds)

The "leaf dip bioassay" used for testing the activity of insecticides against *Bemisia tabaci* (whitefly) biotype B, was similar to that described by Cahill, M et al, Bull. Entomol. Res. 85, 181-187, 1995.

Cotton plants (*Gossypium hirsutum* L.) were grown without any exposure to the insecticides. The leaves were cut up into disc shapes and immersed in an aqueous solution of insecticide containing 0.01% of Agral then left to dry at 25° C. Control leaves were immersed in Agral and distilled water only.

About 20 adult insects were placed onto the small discs of treated cotton leaf.

The insects were allowed to feed and maximum mortality was evaluated at 24 and 48 hours.

By using the formulations prepared as in examples 2 and 3 the results given in table 1 were obtained.

LC50% a.i. and LC99% a.i indicate the quantity of active ingredient (i.e pure insecticide) able to achieve mortality for 50% and 99% of the insects tested.

As a comparison, both the data obtained with imidacloprid and acetamiprid in the absence of the synergistic compound (PBO) and the data obtained with imidacloprid and acetamiprid in a mixture with the same quantity of PBO present in the formulation products of examples 2 and 3 are given in the same table.

The data demonstrate that the formulations of examples 2 and 3 are much more effective than both the corresponding pure insecticides and the mixture of insecticides and synergistic compound.

The resistance factor to imidacloprid was equal to 2336 times that of non-resistant insects.

The resistance factor to acetamiprid was equal to 21 times that of non-resistant insects.

TABLE 1

| Product | LC50% a.i. (*) (ppm) | LC99% a.i. (*) (ppm) |
|---|---|---|
| Acetamiprid | 0.00038 | 0.098 |
| Acetamiprid + PBO mix | 0.00042 | 0.013 |
| Formulation ex. 2 | 0.000078 | 0.00036 |
| Imidacloprid | 4.7 | — |
| Imidacloprid + PBO mix. | 0.019 | 9.7 |
| Formulation ex. 3 | 0.0012 | 0.043 |

(*) a.i. = "active ingredient", being the amount of pure insecticide administered.

The invention claimed is:

1. Supramolecular complex in a cyclodextrin comprising:
   (i) an active principle with insecticidal, acaricidal, fungicidal, snailcidal or vermicidal activity which is selected from the group consisting of pirimicarb, fenazaquin, thiabendazole, pyrimethanil and diazinon, or a neonicotinoid selected from the group consisting of Imidacloprid, Acetamiprid;
   (ii) a synergistic component that is able to synergistically enhance the activity of the active principle (i) selected from the group consisting of piperonyl butoxide, and verbutin; and
   (iii) a cyclodextrin,
   wherein when the synergistic component (ii) is PBO, then the active principle (i) is selected from the group consisting of fenazaquin, thiabendazole, pyrimethanil, diazinon, imidacloprid and acetamiprid; and
   when the synergistic component (ii) is verbutin, then the active principle (i) is selected from the group consisting of pirimicarb, fenazaquin and imidacloprid.

2. Complex as claimed in claim 1, wherein the cyclodextrin is selected from the group consisting of α-cyclodextrin, β-cyclodextrin, γ-cyclodextrin and a hydroxypropyl derivative of β-cyclodextrin.

3. Complex as claimed in claim 1, wherein the quantity of active principle (i) relative to cyclodextrin is between 1% and 50% (weight/weight).

4. Complex as claimed in claim 1, wherein the quantity of active principle (i) relative to cyclodextrin is between 2% and 30% (weight/weight).

5. Complex as claimed in claim 1, wherein the quantity of synergistic component (ii) relative to cyclodextrin is between 0.1% and 100% (weight/weight).

6. Complex as claimed in claim 1, wherein the quantity of synergistic component (ii) relative to cyclodextrin is between 20% and 70% (weight/weight).

7. Complex as claimed in claim 1, wherein the quantity of active principle relative to the synergistic compound is between 0.5% and 7000% (weight/weight).

8. Complex as claimed in claim 1, wherein the quantity of active principle relative to the synergistic compound is between 1% and 1500% (weight/weight).

9. Complex as claimed in claim 1, wherein the quantity of active principle relative to the synergistic compound is between 10% and 70% (weight/weight).

10. Composition with insecticidal, acaricidal, fungicidal, snailcidal or vermicidal activity comprising the supramolecular complex described in claim 1, in combination with a suitable additive and/or carrier.

11. Composition as claimed in claim 10, further comprising an additional synergistic component in free or microemulsified form, wherein the additional synergistic component is the same as or different from the synergistic component present in the supramolecular complex with cyclodextrin.

12. Composition as claimed in claim 11, wherein the quantity of synergistic component in free or microemulsified form is between 0% and 300% (weight/weight).

13. Composition as claimed in claim 10, wherein said composition is formulated as a solid or as a solid/oil composition.

14. Process for preparing the supramolecular complex described in claim 1, comprising the following steps:
    (a) preparing a solution or suspension, in a suitable solvent, of the synergistic component (ii) and the active principle (i), optionally in the presence of a suitable surfactant;
    (b) preparing a solution of cyclodextrin in water or in water/water-miscible organic solvent mixtures;
    (c) adding the solution/suspension obtained in (a) to the solution obtained in (b); and
    (d) maintaining the mixture obtained in (c) under stirring at a temperature between 40° and 90° C. for a time period between 12 and 36 hours.

15. Process as claimed in claim 14, wherein:
    in step (a) the surfactant is present in a quantity up to 12% by weight relative to the synergistic component, and the solvent is an alcoholic solvent
    in step (b), dissolving the cyclodextrin is facilitated by heating to between 50° C. and 90° C. for 30-90 minutes;
    in step (c) the solution/suspension of (a) is added over 2-10 hours, pre-heated to a temperature between 50° and 90° C.; and
    in step (d) the mixture is maintained under stirring, at a temperature between 50° and 75° C. for a period between 18 and 24 hours.

16. Process as claimed in claim 14, wherein the surfactant is present in a quantity between 2% and 4% by weight relative to the synergistic compound, and the solution or suspension in (a) is prepared in ethanol or isopropanol.

17. Process for preparing the supramolecular complex described in claim 1, comprising the following steps:

(a) dissolving the active principle (i) in the synergistic compound (ii), heating the mixture;
(b) preparing a suspension of cyclodextrin in water and heating the suspension to a temperature between 60° and 80° C.;
(c) adding the heated solution obtained in (a) to the heated suspension obtained in (b); and
(d) maintaining the mixture obtained in (c) under stirring at a temperature between 50° and 90° C. for a time period between 1 and 12 hours.

18. Process as claimed in claim 17 wherein:
in step (a) the active principle (i) is dissolved in the synergistic component (ii) at a temperature between 70° and 140° C. in the presence of a suitable surfactant in a quantity up to 12% by weight relative to the synergistic component (ii);
in step (b) the weight/weight percentage of cyclodextrin in water is between 30% and 70%;
in step (c) the solution of (a) is added over a period between 10 and 600 minutes;
in step (d) the mixture is maintained under stirring at a temperature between 70° and 90° C. for a period between 1 and 4 hours.

19. Method for the eradication of insects, mites, moulds, molluscs or worms comprising treating a substrate requiring treatment with the supramolecular complex described in claim 1.

20. Method for the eradication of insects, mites, molds, molluscs or worms characterised by treating a substrate requiring treatment with the composition described in claim 10.

* * * * *